United States Patent
Kanesaka et al.

[11] Patent Number: 6,059,822
[45] Date of Patent: May 9, 2000

[54] STENT WITH DIFFERENT MESH PATTERNS

[75] Inventors: Nozomu Kanesaka; George A. Tashji, both of Hillsdale, N.J.

[73] Assignee: Uni-Cath Inc., Saddle Brook, N.J.

[21] Appl. No.: 08/916,286

[22] Filed: Aug. 22, 1997

[51] Int. Cl.[7] ................................................. A61F 2/06
[52] U.S. Cl. ............................... 623/1; 623/12; 606/198; 606/191
[58] Field of Search ..................... 623/1, 12; 606/108, 606/191, 198

[56] References Cited

U.S. PATENT DOCUMENTS

| | | | |
|---|---|---|---|
| 5,064,435 | 11/1991 | Porter | 623/12 |
| 5,330,500 | 7/1994 | Song | 623/1 |
| 5,383,892 | 1/1995 | Cardon et al. | 623/1 |
| 5,549,663 | 8/1996 | Cottone, Jr. | 623/1 |
| 5,575,818 | 11/1996 | Pinchuk | 623/1 |
| 5,709,713 | 1/1998 | Evans et al. | 623/12 |
| 5,725,547 | 3/1998 | Chuter | 606/194 |
| 5,741,327 | 4/1998 | Frantzen | 623/12 |
| 5,776,183 | 7/1998 | Kanesaka et al. | 623/1 |

*Primary Examiner*—Paul B. Prebilic
*Attorney, Agent, or Firm*—Kanesaka & Takeuchi

[57] ABSTRACT

An expandable reinforcing member with different mesh patterns of the invention is used inside a body lumen, especially, in patient's artery for opening and holding a lesion or stenosis. The stent of the invention includes at least one large mesh portion, and a small mesh portion connected to the large mesh portion. The small mesh portion has a mesh size smaller than that of the large mesh portion. When the stent is delivered into the artery, the small mesh portion is positioned at the lesion or the stenosis, and the large mesh portion is positioned at healthy tissues of the artery. Therefore, the small mesh portion has enough strength to open and hold the lesion or stenosis in the artery, and the large mesh portion does not hurt the healthy tissues of the artery.

5 Claims, 4 Drawing Sheets

STENT WITH DIFFERENT MESH PATTERNS

BACKGROUND OF THE INVENTION AND RELATED ART STATEMENT

The present invention relates to a stent with different mesh patterns, wherein a mesh pattern at least one end of the stent is different from that of a middle portion thereof.

"Stent", which is defined here as a prosthetic member used for reinforcing the blood vessel, has been used in the interluminal vascular treatment in place of surgical exposing, incising, removing, replacing or bypassing a defected blood vessel required in the conventional vascular surgery.

The stent generally has a tubular shape and functions to support a part of a blood vessel or another anatomical lumen from the inside thereof, and is particularly suitable for supporting and holding a dissected arterial lining which may occlude a fluid passageway by collapse thereof.

According to the recent new clinical data, however, the followings have been found as problems upon using the stent.

Firstly, when a stent is placed in a stenosis, it extends over the full length of the stenosis. Namely, a stent is placed to bridge the whole lesion starting from a healthy tissue, lesion, and then to another healthy tissue. When a stent, normally made of metal, contacts the coronary wall, micro thromboses may occur at the contact areas with healthy tissues. As a result, when the stent is placed to open and hold the lesion, there are more chances of thromboses occurring at both ends of the stent corresponding to the healthy tissues. This is because all stents currently known have a uniform pattern throughout the entire length thereof, i.e. the strength and expandability are the same throughout the entire length of the stent, including the healthy tissues.

In view of the formation of micro thromboses, the stent with less metal contact is preferable. However, it is also necessary to have more metal coverage against prolapse, i.e. excessive tissue growth passing through the stent.

Secondly, in the balloon expandable type of the stent, the stent in a closed condition is mounted on the balloon section of the balloon catheter, and delivered to the lesion or stenosis by the balloon catheter. When the stent in the closed condition has the same diameter throughout the entire length thereof and delivered through a meandering artery in and around the calcified lesion, a front end of the stent might be caught at the calcified lesion if the diameter at the end is not small enough for passing through the calcified lesion or the narrow artery.

In this respect, if the diameter of the stent in the closed condition is small, it is possible to pass the narrow artery. However, when the stent is expanded to have a large diameter, the expanded stent can not sufficiently support. On the other hand, if the expanded stent is made to sufficiently support the artery, the stent must have a large number of supports, so that the stent can not be expanded to have a large diameter.

Therefore, there is no conventional stent expandable by a balloon catheter, which has a sufficient support structure; can expand to have a large diameter; and can pass the narrow artery.

Accordingly, one object of the invention is to provide a stent in which a middle portion thereof has enough or maximum strength to open and hold the stenosis or lesion.

Another object of the invention is to provide a stent as stated above, wherein end portions of the stent do not hurt healthy tissues of the artery.

A further object of the invention is to provide a stent as stated above, which can be easily delivered through the meandering and narrow artery without being caught at the calcified lesion or the narrow artery.

Further objects and advantages of the invention will be apparent from the following description of the invention.

SUMMARY OF THE INVENTION

To achieve the aforementioned objects, the invention provides an expandable reinforcing member or stent used inside a body lumen, including a large mesh portion located at least one end of the reinforcing member and having a plurality of strands; and a small mesh portion located in a middle of the reinforcing member and having a plurality of strands. In the expandable reinforcing member of the invention, the small mesh portion is integrally connected to the large mesh portion at the end thereof, and the small mesh portion has the strands with a number larger than that of the strands of the large mesh portion.

Preferably, the small mesh portion is located between the large mesh portions. When the reinforcing member is formed, the stent has the constant diameter throughout the entire length thereof. Therefore, the small mesh portion has spaces less than the large mesh portions.

The reinforcing member of the invention is disposed over a balloon catheter and is delivered to a desired portion inside the body lumen. Also, the reinforcing member is expanded by the balloon catheter.

When the reinforcing member or stent is used, the reinforcing member is disposed on the balloon catheter. Then, the large diameter portions are pushed over balloon catheter such that both ends of the reinforcing member have the diameter smaller than that at the middle portion, i.e. small mesh portion. Accordingly, the stent can relatively easily pass through the meandering and narrow artery when the reinforcing member is delivered by the balloon catheter.

After the reinforcing member is delivered to a specific portion of the artery, the balloon is expanded to enlarge the reinforcing member. As a result, the small and large mesh portions are substantially equally expanded. The diameter of the reinforcing member in the expanded state is substantially the same throughout the entire length thereof.

Since the lesion is supported by the small mesh portion, the lesion is well supported by the reinforcing member. Since the large mesh portions which have supporting strength less than that of the small mesh portion are located under the healthy tissues, the supporting strength is not degraded by the large mesh portions. Also, since the large mesh portions contact the healthy tissues, the contact areas of metal are reduced. Possibility of forming micro thromboses and vessel injury is reduced.

Preferably, the large mesh portion may be formed of at least one row of first joint members and at least two rows of first flexible elongated members. The small mesh portion can be also formed of plural rows of second joint members and plural rows of second elongated members. Each first elongated member is longer than each second elongated member, and the number of the first elongated members is less than that of the second elongated members.

Still further, in the stent formed of the second joint members and the second flexible elongated members, each row of the second elongated members is situated between adjacent two rows of the second joint members and arranged circularly around the central axis. Also, the second elongated members in each row are inclined substantially in the same direction and diagonally with an acute angle with respect to a line on a surface of the reinforcing member parallel to the central axis of the reinforcing member. The second elongated members in two rows sandwiching one row of the second joint members are arranged substantially symmetrically relative to the one row of the second joint members. Accordingly, when a radial force is applied from an inside of the reinforcing member, the second elongated members are expanded relative to the second joint members to have an obtuse angle with respect to the aforementioned line on the surface of the reinforcing member to thereby allow the reinforcing member to have a second diameter larger than the first diameter.

Preferably, the second diameter is two to five times larger than the first diameter.

DETAILED DESCRIPTION OF PREFERRED EMBODIMENTS

A first embodiment of the present invention will be explained with reference to FIGS. 1 through 4.

Figure 1:
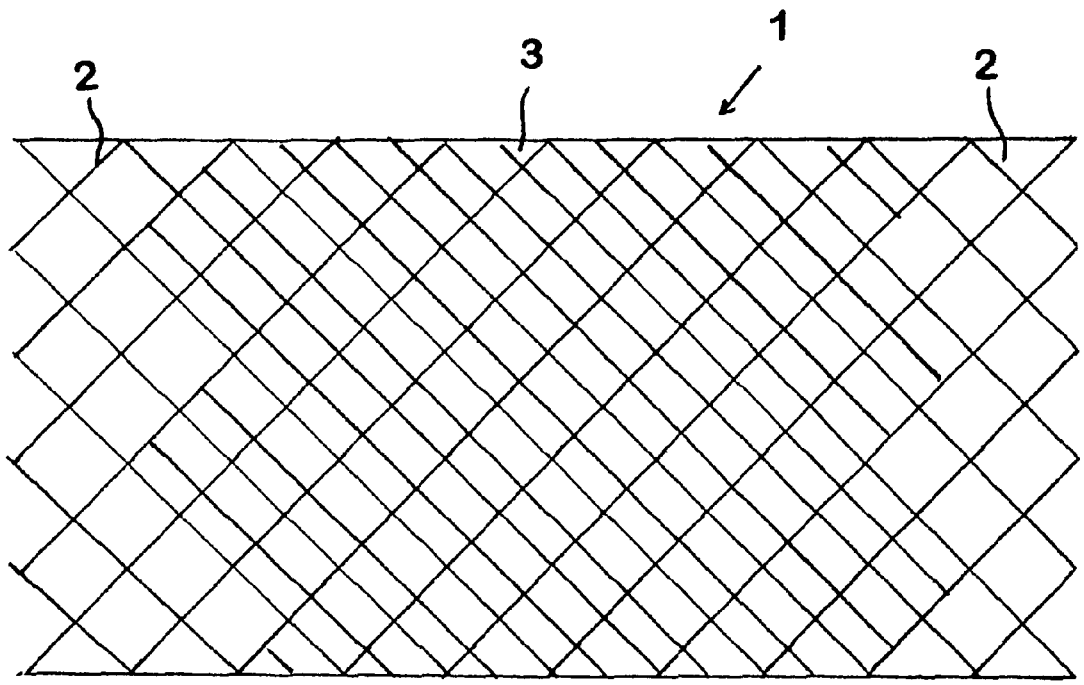
FIG. 1 is an explanatory plan view of a stent in a flat sheet form according to a first embodiment of the present invention.
Figure 2:
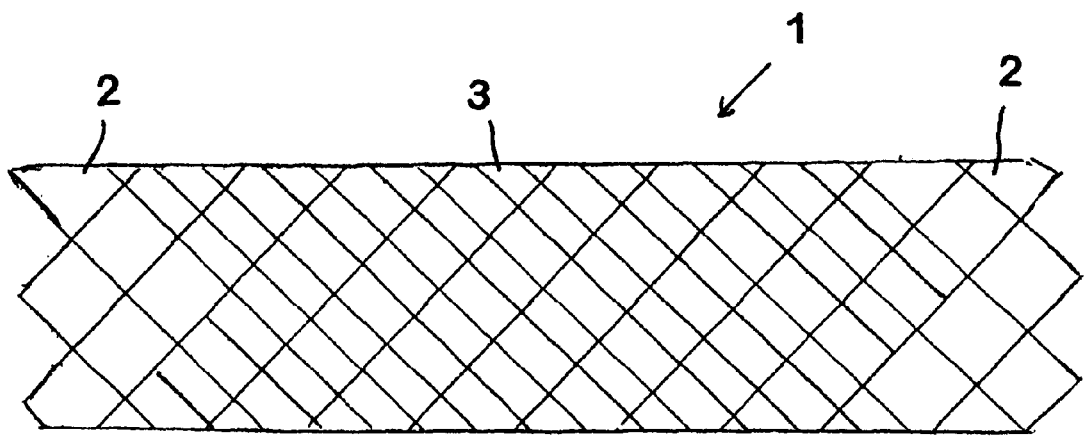
FIG. 2 is an explanatory side view of the stent in a circular form.

Numeral 1 designates a stent of a first embodiment of the invention, and the stent 1 has a cylindrical shape having a mesh pattern as shown in a plan view of FIG. 1 cut into a flat sheet form. The stent has large mesh portions 2 at both ends thereof, and a small mesh portion 3 having size comparatively smaller than that of the large mesh portions 2. The small mesh portion 3 constitutes a middle portion of the stent between the large mesh portions 2, as shown in FIG. 2.

Namely, a mesh size of the stent 1 is varied from the center to the ends of the stent. A smaller mesh size is used in the center of the stent, where the main lesion is located in order to have a more metal coverage when the stent 1 is introduced in the artery. The small mesh portion 3 provides more radial strength and lessens a chance of prolapse, which is a growth of unwanted tissues. Both ends of the stent 1, which are usually positioned on the healthy artery wall, have a larger mesh size. This will help reducing micro lesions on the healthy tissue where neither high metal coverage nor radial strength is required.

Figure 3:
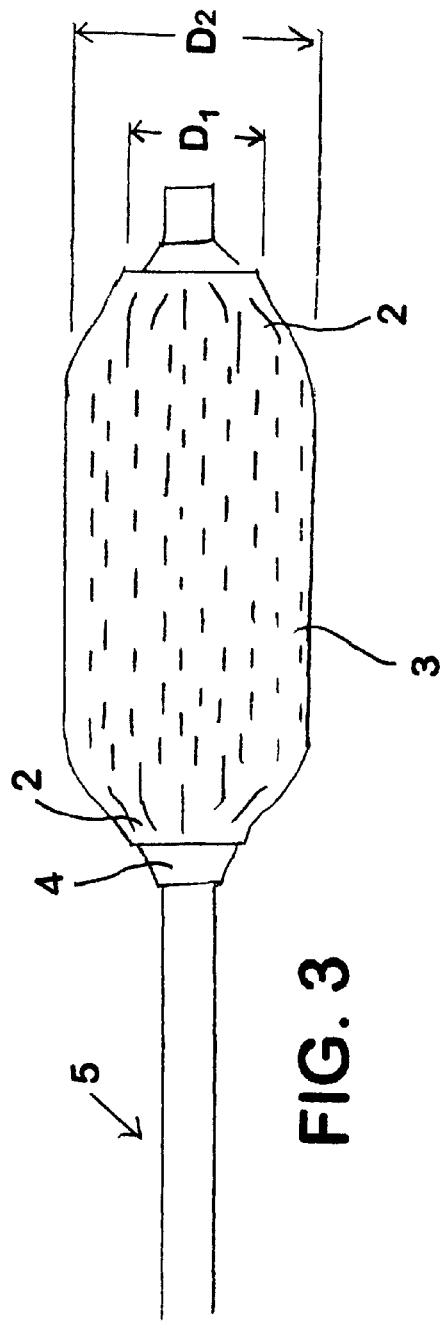
FIG. 3 is a side view of the stent mounted on a balloon catheter.

The stent 1 of the invention is delivered and expanded by a balloon catheter, which is known in the art, to thereby locate the stent 1 in the desired location in the artery, such as a lesion. As shown in FIG. 3, the collapsed stent 1 is mounted on a balloon section 4 of a balloon catheter 5. Namely, when the stent 1 is mounted on the balloon section 4, both ends of the stent are pushed or squeezed inwardly to have a shape like a football because of the larger mesh size thereof. This minimizes the exposure of the edges. Since a shape of the stent 1 in the collapsed condition is like a football, when the stent 1 mounted on the balloon catheter 5 is being delivered in the meandering narrow body lumen, such as an artery, the forward end of the stent 1, i.e. large mesh portion 2, is not caught on the narrow part, such as the calcified lesion. Therefore, the stent 1 can be delivered in and around the lesion easily.

Figure 4:
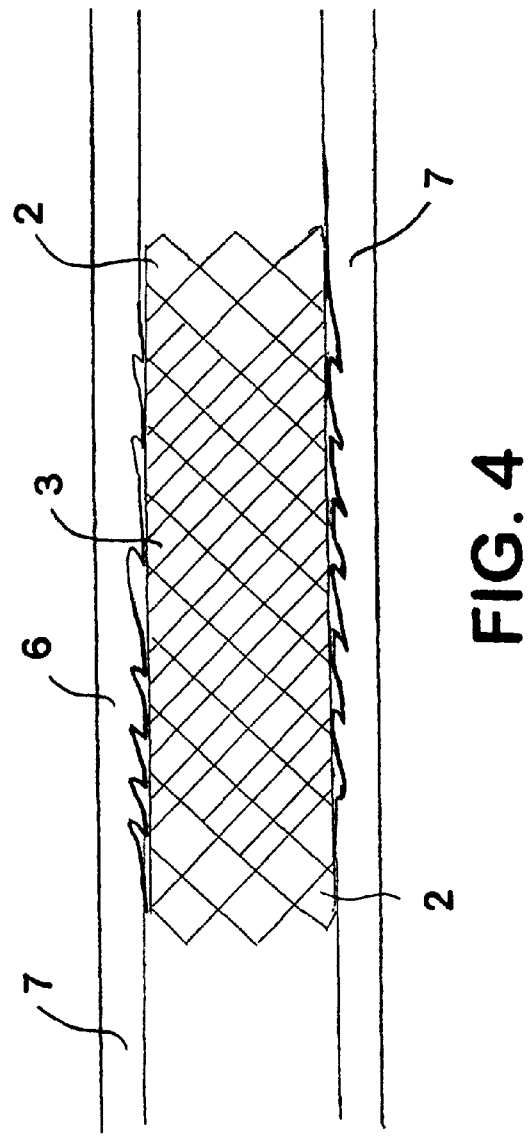
FIG. 4 is a side view of the stent in an expanded condition in the artery.

When the stent 1 is located in and around a lesion 6 by the balloon catheter 5, the balloon section 4 is inflated to expand the stent 1 to be a condition as shown in FIG. 4, so that the stent 1 has the same diameter throughout the entire length. Since the ends of the stent 1 are formed of the large mesh portions 2, the strength at the ends is not strong or excessive as compared to the middle portion of the stent 1 formed of the small mesh portion 3. As shown in FIG. 4, the small mesh portion 3 of the middle portion has enough strength to open and hold the lesion 6 of the artery, and the large mesh portions 2 do not hurt healthy tissue parts 7 of the artery since the strength at the large mesh portions 2 is not excessive.

In regard to the mesh size, length and dimension, they may be selected as desired as long as the forward end of the stent 1 has the mesh size larger than that at the middle portion when it is installed on the balloon catheter. Preferably, when the stent 1 is installed on the balloon catheter, the diameter $D_1$ of the stent 1 at the large mesh portion 2 is half of the diameter $D_2$ of the stent 1 at the small mesh portion 3.

Figure 5:
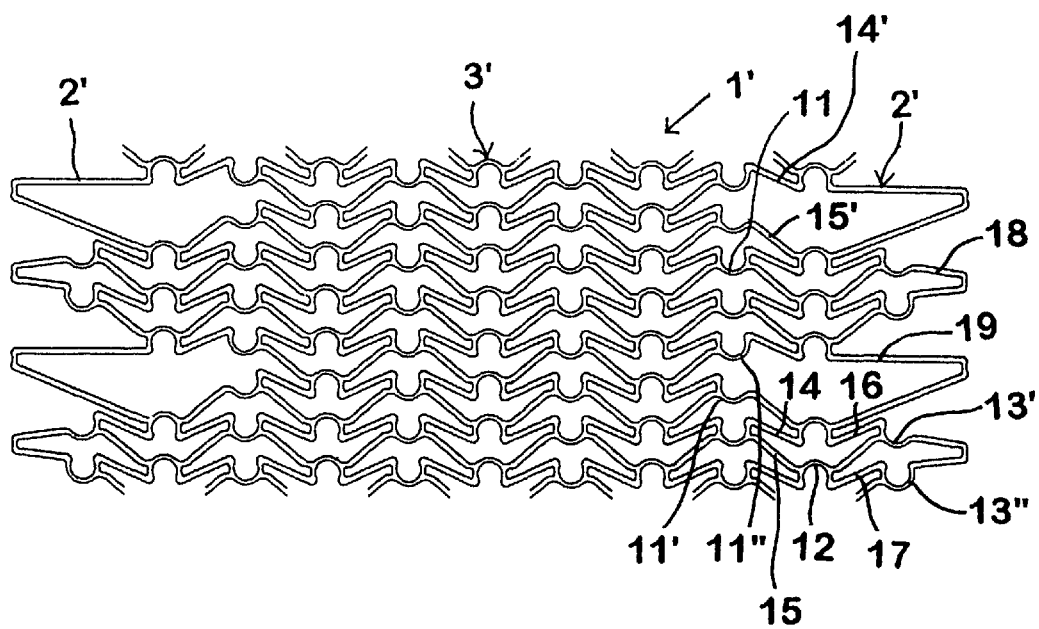
FIG. 5 is a plan view of a stent in a flat sheet form according to a second embodiment of the invention.

By referring to FIGS. 5 through 7, a second embodiment of the invention will be explained as follows. As shown in FIG. 5, a stent 1' of the second embodiment of the invention has a cylindrical shape having a mesh pattern as shown in a plan view of FIG. 5 cut into a flat sheet form. The stent 1' also has a small mesh portion 3' and large mesh portions 2'. The small mesh portion 3' is formed of U-shaped joint members 8, and elongated members 9, 10 connected to both sides of the joint member 8. The U-shaped joint members are arranged circularly around a center axis of the stent 1' and are spaced along the center axis thereof. The elongated members 9, 10 in one joint member 8 are connected to two joint members 8 adjacent thereto.

The large mesh portion 2' is formed of U-shaped joint members, and elongated members, similar to the small mesh portion 3'. However, the shape and the arrangement of the U-shaped joint members and the elongated members are slightly different. Namely, the U-shaped joint members have joint members 11, 12 same as the joint member 8, and joint members 11', 11", 13', 13". The joint members 11', 13' are the same, and the joint members 11", 13" are the same. The elongated members have short elongated members 14, 14', 15, 15', 16, 17, 18, and long elongated members 19. The short elongated members 14, 15, 16, 17 are the same as the elongated members 9, 10. The short elongated members 14, 14', 15, 15' are disposed among the joint members 11, 11', 12, and the short elongated members 16, 17 are disposed among the joint members 12, 13', 13". The long elongated members 19 extend from the joint members 12, and the short elongated members 18 extend from the joint members 13', 13".

Figure 6:
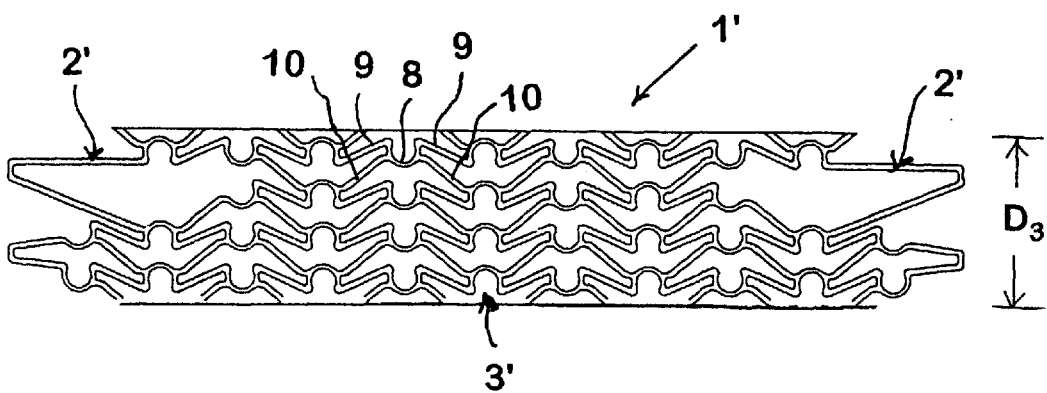
FIG. 6 is an explanatory side view of the stent in a circular form.

As shown in FIGS. 5 and 6, the large mesh portion 2' is formed similar to the small mesh portion 3', from which parts of the joint members 8 and the elongated members 9, 10 are removed. The small mesh portion 3' of the stent 1' has similar structure and operation as in U.S. patent application Ser. No. 08/702,167 filed on Aug. 23, 1996, and the stent of the aforementioned application is referred to in the application.

Also, the stent 1' is mounted over the balloon catheter as in the first embodiment, and delivered through the meandering and narrow artery. When the stent 1' in a closed condition is mounted on the balloon catheter, the diameter at the large mesh portion 2', i.e. the end of the stent 1', is also smaller than that of the small mesh portion 3', i.e. the middle portion of the stent 1', as in the first embodiment, so that the stent 1' can be delivered to the lesion easily and smoothly.

Figure 7:
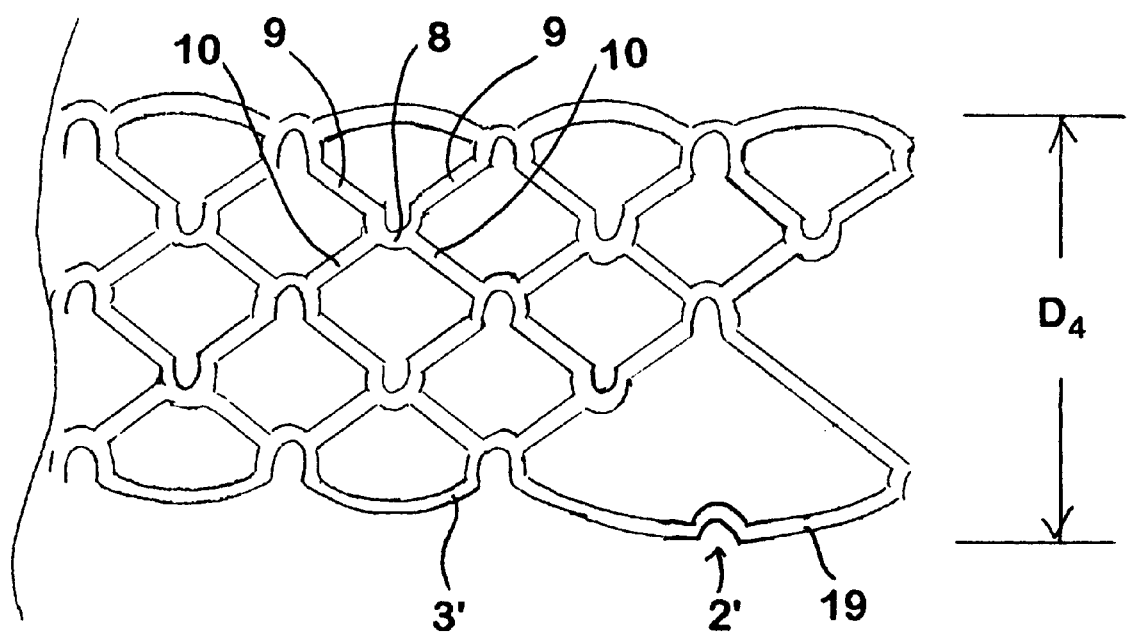
FIG. 7 is an enlarged explanatory side view of a part of the stent in an expanded form of the second embodiment of the invention.

When the stent 1' is expanded, the elongated members connected to the ends of the joint member expand mainly so as to become the expanded condition as shown in FIG. 7. Preferably, the stent 1' is constructed such that the diameter $D_3$ of the stent 1' in the closed condition is one-forth of the diameter $D_4$ of the stent 1' in the expanded condition.

Although in the embodiments of the invention, a variable mesh pattern was used to construct the stent, a variable spiral pattern can be alternatively used to construct the stent.

Also, the stent can be coated with Dedication anti-coagulant such as heparin.

Further, the stent can be coated with polymer, so that blood becomes difficult to be coagulated. Preferably, the stent is coated with polymer impregnated with medication.

Furthermore, the stent can be mace of metal with spring ability or memory expanding metal for self expansion.

According to the present invention, since the stent has variable mesh sizes at the middle portion and end portions, in other words, the end portions have a mesh size larger than that of the middle portion, when the stent is expanded in the artery, the stent has enough strength at the middle portion corresponding to the lesion to thereby open and hold the same, and also the end portions of the stent corresponding to the location of the healthy tissues in the artery have appropriate strength, which is not so strong as that of the middle portion. Therefore, the stent of the invention can successfully open and hold the lesion, and at the same time, the ends of the stent do not hurt the healthy tissues.

Also, according to the present invention, when the stent is disposed or collapsed on the balloon catheter, a shape of the stent is like a football having tapered ends thereof. Therefore, while the stent is being delivered into the lesion through the meandering artery, the ends of the stent are not caught anywhere, especially at the calcified lesion, so that the stent can be delivered to the desired location easily.

While the invention has been explained with reference to the specific embodiments of the invention, the explanation is illustrative and the invention is limited only by the appended claims.

What is claimed is:

1. An expandable reinforcing member, comprising:
    two large cylindrical mesh portions located at two longitudinal end areas of the reinforcing member, each of the large mesh portions being collapsible to taper laterally outwardly of the reinforcing member and being formed of circularly arranged radially aligned first joint members and circularly arranged radially aligned first elongated members connected to the first joint members, and
    a small cylindrical mesh portion situated between the two large mesh portions and integrally connected to the two larger mesh portions as one unit in a plurality of radially aligned rows, said smaller mesh portion being formed of plural radially aligned rows of circularly arranged second joint members and plural radially aligned rows of circularly arranged second elongated members, each row of said second elongated members having a number of second elongated members larger than that of the first elongated members of each of the large mesh portions, some of said first elongated members being at least longer than each of said second elongated members.

2. An expandable reinforcing member comprising:
    at least one large mesh portion located on one side of the reinforcing member and having a plurality of strands, said at least one larger mesh portion being formed of circularly arranged first joint members and circularly arranged first elongated members connected to the first joint members, and
    a small mesh portion connected to the at least one large mesh portion and having a plurality of strands with a number larger than that of the strands of the large mesh portion, said small mesh portion being formed of plural rows of circularly arranged second joint members and plural rows of circularly arranged second elongated members, some of said first elongated members being at least longer than each of said second elongated members,
    said each row of the second elongated members being situated between adjacent two rows of the second joint members and arranged circularly around a central axis of the reinforcing member, said second elongated members in each row being inclined substantially in a same direction and diagonally with an acute angle with respect to a line on a surface of the reinforcing member parallel to the central axis of the reinforcing member, each of said second elongated members connecting two of the second joint members situated in adjacent two rows of the second joint members, said second elongated members in two rows sandwiching one row of the second joint members being arranged substantially symmetrically relative to said one row of the second joint members so that when a radial force is applied from an inside of the reinforcing member, the second elongated members are expanded relative to the second joint members to have an obtuse angle with respect to said line on the surface of the reinforcing member to thereby allow the reinforcing member to have a second diameter larger than a first diameter.

3. An expandable reinforcing member according to claim 2, wherein said expandable reinforcing member includes two large mesh portions disposed at two lateral ends of the small mesh portion.

4. An expandable reinforcing member according to claim 2, wherein said reinforcing member has a cylindrical shape, and the large mesh portion is collapsible to taper from the small mesh portion.

5. An expandable reinforcing member according to claim 2, wherein the second diameter of the reinforcing member is about four times larger than the first diameter.

* * * * *